US010444228B2

(12) United States Patent
Guillouzo

(10) Patent No.: US 10,444,228 B2
(45) Date of Patent: Oct. 15, 2019

(54) METHOD OF SCREENING A CANDIDATE COMPOUND FOR INDUCING BILE CANALICULAR FUNCTION DISORDERS

(71) Applicant: Biopredic International, Saint-Gregoire (FR)

(72) Inventor: Christiane Guillouzo, Rennes (FR)

(73) Assignee: Biopredic International, Saint-Gregoire (FR)

( * ) Notice: Subject to any disclaimer, the term of this patent is extended or adjusted under 35 U.S.C. 154(b) by 0 days.

(21) Appl. No.: 15/505,489

(22) PCT Filed: Aug. 22, 2014

(86) PCT No.: PCT/IB2014/001843
§ 371 (c)(1),
(2) Date: Feb. 21, 2017

(87) PCT Pub. No.: WO2016/027117
PCT Pub. Date: Feb. 25, 2016

(65) Prior Publication Data
US 2017/0269065 A1 Sep. 21, 2017

(51) Int. Cl.
G01N 33/50 (2006.01)

(52) U.S. Cl.
CPC ..... *G01N 33/5067* (2013.01); *G01N 33/5026* (2013.01); *G01N 33/5035* (2013.01); *G01N 2333/96494* (2013.01); *G01N 2800/08* (2013.01)

(58) Field of Classification Search
CPC .......... G01N 33/5067; G01N 33/5035; G01N 33/5026; G01N 2800/08; G01N 2333/96494
See application file for complete search history.

(56) References Cited

U.S. PATENT DOCUMENTS

2005/0048464 A1  3/2005  Tian et al.
2006/0234332 A1  10/2006  Mattheakis et al.

FOREIGN PATENT DOCUMENTS

JP  H08503610  4/1996
WO  2013158939  10/2013

OTHER PUBLICATIONS

Kono et al. Effects of Cholestatic Agents on the Structure and Function of Bile Canaliculi in Neonatal Rat Hepatocytes in Primary Culture. Tohoku J. Exp. Med., 1997, 181, p. 9-18 (Year: 1997).*
Soldatow et al. In vitro models for liver toxicity testing. Toxicol Res (Camb). Jan. 1, 2013; 2(1): 23-39. (Year: 2013).*
Leite et al. Three-Dimensional HepaRG Model as an Attractive Tool for Toxicity Testing. toxicological sciences 130(1), 106-116 (2012) (Year: 2012).*
Office Action in corresponding European Patent Application Serial No. 14809503.7, dated Feb. 28, 2018.
Horikawa, et al., "Potential Cholestatic Activity of Various Therapeutic Agents Assessed by Bile Canalicular Membrane Vesicles Isolated from Rats and Humans", Drug Metab. Pharmacokin., Jan. 8, 2003, vol. 18, issue 1, pp. 16-22.
Office Action in corresponding Japanese Patent Application Serial No. JP 2017-529161, dated May 22, 2018.
Vermeer, et al., "MMP9 modulates tight junction integrity and cell viability in human airway epithelia", Am J Physiol Lung Cell Mol Physiol., May 2009, vol. 296, issue 5, pp. L751-L762.
Palakkan, et al., "An In Vitro Fluorometric Assay for Evaluating Functional Polarity of Hepatocyte", International J of Bioassays, Jan. 2014, vol. 3, issue 1, pp. 1630-1636.
Chatterjee, et al., "Hepatocyte-based in vitro model for assessment of drug-induced cholestasis", Toxicol Appl Pharmacol., Jan. 2014, vol. 274, issue 1, pp. 124-136.
Herrema, et al., "Rho Kinase, Myosin-II, and p42/44 MAPK Control Extracellular Matrix-mediated Apical Bile Canalicular Lumen Morphogenesis in HepG2 Cells", Molecular Bio. of the Cell, Jul. 2006, vol. 17, issue 7, pp. 3291-3303.
Liao, et al., "RhoA/Rho-Kinase and Nitric Oxide in Vascular Reactivity in Rats with Endotoxaemia", PLOS One, Feb. 15, 2013, vol. 8, issue 2, 14 pages.
International Search Report and Written Opinion in corresponding PCT Patent Application Serial No. PCT/IB2014/001843 dated Jul. 14, 2015, 16 pages.
Padda, et al.,"Drug Induced Cholestasis", Hepatology, Apr. 2011, vol. 53, issue 4, pp. 1377-1387.
Watanabe, et al., "Ca2+ causes active contraction of bile canaliculi: Direct evidence from microinjection studies", Proc. Natl. Acad. Sci., Oct. 1984, vol. 81, pp. 6164-6168.
Anthérieu, et al., "Oxidative Stress Plays a Major Role in Chlorpromazine-Induced Cholestasis in Human HepaRG Cells" Hepatology, Apr. 4, 2013, vol. 57, issue 4, pp. 1518-1529.
Kumary, et al., "An In Vitro Fluorometic Assay for Evaluating Functional Polarity of Hepatocyte", Inter. J. of Bioassays, Mar. 21, 2014, vol. 3, issue 1, pp. 1630-1636.
Phillips, et al., "A Study of Bile Canalicular Contractions in Isolated Hepatocytes", Hepatology, 1982, vol. 2, issue 6, pp. 763-768.
Galli, et al., "Oxidative Stress Stimulâtes Proliferation and Invasiveness of Hepatic Stellate Cells via a MMP2-Mediated Mechanism", Hepatology, May 5, 2005, vol. 41, issue 5, pp. 1074-1084.
Office Action in corresponding European Patent Application Serial No. 14809503.7, dated Oct. 22, 2018.
Office Action in corresponding Japanese Patent Application No. 2017-529161, dated Mar. 31, 2019 (English machine translation attached).

(Continued)

*Primary Examiner* — Taeyoon Kim
(74) *Attorney, Agent, or Firm* — Hovey Williams LLP

(57) ABSTRACT

In vitro methods and kits for modulating and studying mechanical movement of hepatic bile canaliculi lumen through activation or inhibition of the Rho-kinase molecular regulation pathway. In vitro methods and kits for modulating lumen opening and clearing using matrix metalloproteinases, as well as diagnostic methods based upon the same.

18 Claims, 10 Drawing Sheets

(56) References Cited

OTHER PUBLICATIONS

Overall, "Molecular determinants of metalloproteinase substrate specificity" Molecular Biotechnology, Sep. 2002, vol. 22, Issue 1, pp. 51-86.
Nagase, "Substrate Specificity of MMPs" Matrix Metalloproteinase Inhibitors in Cancer Therapy, pp. 39-66, 2001.
Murphy, et al., "Progress in matrix metalloproteinase research", Mol Aspects Med. Oct. 2008; 29(5): 290-308.
Kridel, et al., "Substrate hydrolysis by matrix metalloproteinase-9", J Biol Chem., vol. 276, issue 23, Jun. 8, 2001.

* cited by examiner

METHOD OF SCREENING A CANDIDATE COMPOUND FOR INDUCING BILE CANALICULAR FUNCTION DISORDERS

RELATED APPLICATIONS

This application is the National Stage of International Patent Application No. PCT/IB2014/001843, filed Aug. 22, 2014, which is hereby incorporated by reference in its entirety.

BACKGROUND OF THE INVENTION

Field of the Invention

The present invention concerns the repeated mechanical movements of swelling and contraction of bile canaliculi lumen making possible the canalicular lumen clearing, and the relationship with the Rho-kinase pathway and myosin light chain phosphorylation for molecular regulation of these movements. The invention also extends to cholestatic diseases with evidence of disorders in these movements associated with alteration of the Rho-kinase pathway activity and permeability of parajunctional spaces conditioning the lumen clearing. The invention is also concerned with methods for detection of these alterations and using derivatives for screening candidate compounds for susceptibility to induce canalicular functional activity, and for detecting diseases associated with biliary flow dysfunctions.

Description of Related Art

Cholestasis is a condition where bile cannot flow from the liver to the duodenum. A key functional parameter for good bile flow from hepatocytes is contraction of the bile canaliculi. Acute and chronic cholestasis results from dysfunction of the normal mechanisms of bile formation. Several forms of cholestatic disease can be produced by drugs. For example, chlorpromazine (CPZ) is known to induce intrahepatic cholestasis in vivo. The effect was also described in human HepaRG® cells in vitro, with evidence of occurrence of bile canaliculi constriction. Several cases of cholestatic side effects have been reported with new drugs during the last few years. Therefore, the urgent challenge today is to increase the ability to improve the safety of therapeutics by better predicting these drug-induced adverse effects. For many concerned drugs the proposed explanation has mainly involved alteration of the hepatobiliary transport system, in particular reduction of available bile salt export pump molecules. A role for oxidative stress as a primary causal agent and/or an aggravating factor has also been supported by research. Concomitantly, other mechanisms such as cytoskeletal modifications and disruption of cell-to-cell junctions, all known to participate to cell polarity could be involved in altered bile salt flow in cholestasis. However, molecular mechanisms controlling this cascade of events in hepatocytes are poorly understood. FIG. 1 shows the hepatic lobule organization in liver tissue. FIG. 2 shows the junctional complex around the canalicular lumen, and the organization of a tight junction and localization of junction proteins.

Models and methods for detecting and characterizing drug-associated cholestatic disorders have been attempted. One problem relates to finding suitable hepatic models for in vitro studies. Hepatocyte polarization with bile canalicular formation is a complex mechanism which includes cytoskeletal, tight junctional and intracellular trafficking components. Limited availability of human fresh cells has led to use human cell lines. Generally permanent hepatic cell lines fail to form typical networks of bile canaliculi as in vivo and consequently, knowledge on the signaling pathways involved in bile canalicular lumen constriction and enlargement remains poor. Previous studies used WIFB9 or human HepG2 cells to describe the cell polarity and an interesting demonstration of the major role exerted by extracellular matrix signaling onto the canalicular formation using multilayered hepatic cords experimentally built with HepG2 cells, has been reported. However, these cells express only few functions characterizing the mature hepatocyte detoxification metabolism, including transport function. In contrast, recent research has indicated that differentiated human HepaRG cells which express phases 1 and 2 drug metabolizing enzymes and transporters, and form bile canaliculi structures, can be used to mimic features of intrahepatic cholestasis induced by CPZ treatment and to characterize the mechanisms involved in the initiation of the lesions. Bile canaliculi constriction and H2O2 production were mainly evidenced (Antherieu S. et al., 2013).

Methods have been established for analyzing cholestatic disorders. The general assumption up to now was that the major disorder expected to occur in cholestatic disorders was alteration of the hepatobiliary transport system associated with reduction of the number of available bile salt export pump molecules due to inhibition or competition between candidate compounds and bile salts. Thus, the general strategy for detection exclusively focused on:

i)—a study on levels of transporters expression and search for drug binding onto target transporters;

ii)—evidence and calculation of drug efflux alteration mainly using the radiolabelled bile salt precursor taurocholate as referent marker candidate (See e.g., U.S. Pat. No. 7,604,934).

This test consists in defining the bile efflux index using the following equation:

$$BEI = \frac{\text{Accumulation Plus}(+)\text{Buffer} - \text{Accumulation Minus}(-)\text{Buffer}}{\text{AccumulationPlus}(+)\text{Buffer}} \times 100$$

Total accumulation of radiolabelled taurocholate determined in HBSS Plus (+) buffer representing the total mass of compound taken up and excreted whereas the total mass of analyte inside the cells at the end of incubation is determined in Minus (−) buffer. (+) buffer is a Ca++ buffer and (−) buffer is Ca++-free buffer.

However, such assays have drawbacks. The main limitations of such assays are that: i)—it is designed primarily for studying biliary efflux of the candidate compounds and not necessarily the bile flow out the canaliculi; ii) it considers only the flow from the hepatocytes toward the bile canaliculi, and does not take into account the emptying of that bile canaliculi; iii)—Transporters, principally BSEP, are considered as the main factors involved in the modulation of biliary excretion; and iv)—it does not consider dynamic events of contraction/relaxation associated with efflux and clearing. Thus, it fails to highlight some important biological effects. For instance, there is no consideration of possible modification of the canalicular lumen (size) and analysis of mechanical activity (contractile movements) of bile canaliculi conditioning canalicular lumen clearing; v)—Index calculation is an endpoint; vi)—another limitation is the use of human primary cultures which have a limited lifetime even when they are used under sandwich conditions. In addition, reproducibility is always questionable due to known inter-individual variability.

SUMMARY OF THE INVENTION

The present invention is broadly concerned with in vitro methods, assays, kits, and processes. In one or more embodiments, an in vitro method of screening a candidate compound for inducing bile canalicular function disorders is disclosed. The method comprises exposing a cell culture to the candidate compound, wherein the cell culture comprises a cell culture medium, hepatocytes and a bile canalicular structure having a biliary space characterized by a lumen; and detecting morphological alterations of the biliary space.

Further methods are disclosed herein. In one or more embodiments, the method comprises exposing a cell culture to the candidate compound, wherein the cell culture comprises a cell culture medium, hepatocytes and a bile canalicular structure having a biliary space characterized by a lumen. The cell culture is washed after exposing to the candidate compound. The washed cell culture is then exposed to a marker compound for accumulation into the biliary space to yield cell culture with accumulated marker compound. The cell culture with accumulated marker compound is then washed, followed by exposing to activated matrix metalloproteinase, and detecting and quantifying release of the marker compound into the culture medium.

In one or more embodiments, the method comprises exposing a cell culture to the candidate compound, wherein the cell culture comprises a cell culture medium, hepatocytes and a bile canalicular structure having a biliary space characterized by a lumen. The cell culture is washed after exposing to the candidate compound. The washed cell culture is then exposed to a marker compound and activated matrix metalloproteinase for accumulation into the biliary space to yield cell culture with accumulated marker compound. The cell culture with accumulated marker compound is then washed, followed by incubating the cell culture for marker compound accumulation in the culture medium. The cell culture is then disrupted with nonionic surfactant, such as polyethylene glycol p-(1,1,3,3-tetramethylbutyl)-phenyl ether, to completely release the dye/marker compound. The release of the marker compound is then detected as quantified.

Also disclosed herein is the use of a Rho-kinase pathway activator or inhibitor to modulate mechanical movement of bile canaliculi lumen through activation or inhibition of the Rho-kinase molecular regulation pathway.

A method of modulating mechanical movement of bile canaliculi lumen is also described herein. The method comprises providing a cell culture comprising a cell culture medium, hepatocytes and a bile canalicular structure having a biliary space characterized by a lumen, and exposing the cell culture to an inhibitor or activator of the Rho-kinase pathway.

An in vitro method of modulating hepatic biliary polarity and differentiation in culture is also disclosed. The method comprises providing a cell culture of hepatic cells, and exposing the cell culture to an activator of Rho-kinase to yield differentiated hepatic cells.

A kit for screening a candidate compound for inducing bile canalicular function disorders is also described herein. The kit comprises polarized mature hepatic cells (e.g., differentiated HepaRG cells), F-actin; a marker compound (e.g., large or small molecule fluorescent dye or substrate), matrix metalloproteinase, and a matrix metalloproteinase activator. Instructions for using the kit according to the assays described herein can also be included.

Also disclosed herein is a kit for screening a candidate compound for inducing bile canalicular function disorders in presence or absence of a target transporter. The kit comprises The kit comprises polarized mature hepatic cells (e.g., differentiated HepaRG cells), F-actin; a marker compound (e.g., large or small molecule fluorescent dye or substrate), matrix metalloproteinase, and a matrix metalloproteinase activator, along with engineered hepatic cells derived from the polarized mature hepatic cells, which a knock-out for the particular target transporter to be studied.

Also disclosed herein is the use of a metalloproteinase to modulate lumen opening and clearing on an in vitro culture comprising hepatic cells and a bile canalicular structure having a biliary space characterized by a lumen.

A method of modulating lumen opening and clearing in vitro is also described herein. The method comprises providing a cell culture comprising a cell culture medium, hepatocytes and a bile canalicular structure having a biliary space characterized by a lumen. The cell culture is exposed to an activator of Rho-kinase, wherein the bile canaliculi lumen contracts after the exposing. The cell culture is exposed to activated matrix metalloproteinase, wherein said lumen is opened and cleared after the exposing.

A method of diagnosing cholestasis in a patient is also described. The method comprises providing a biological sample collected from the patient analyzing the biological sample for matrix metalloproteinase, wherein matrix metalloproteinase present in the sample is a marker indicating obstructive cholestasis.

DETAILED DESCRIPTION OF PREFERRED EMBODIMENTS

Figure 1:
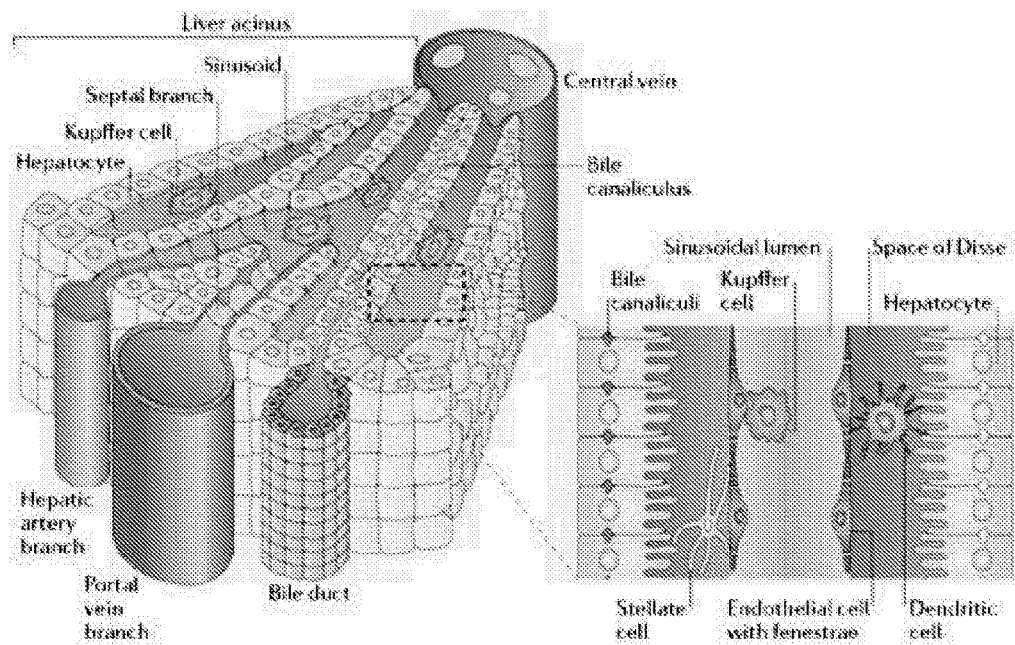
FIG. 1 is an illustration of the hepatic lobule organization in liver tissue.
Figure 2:
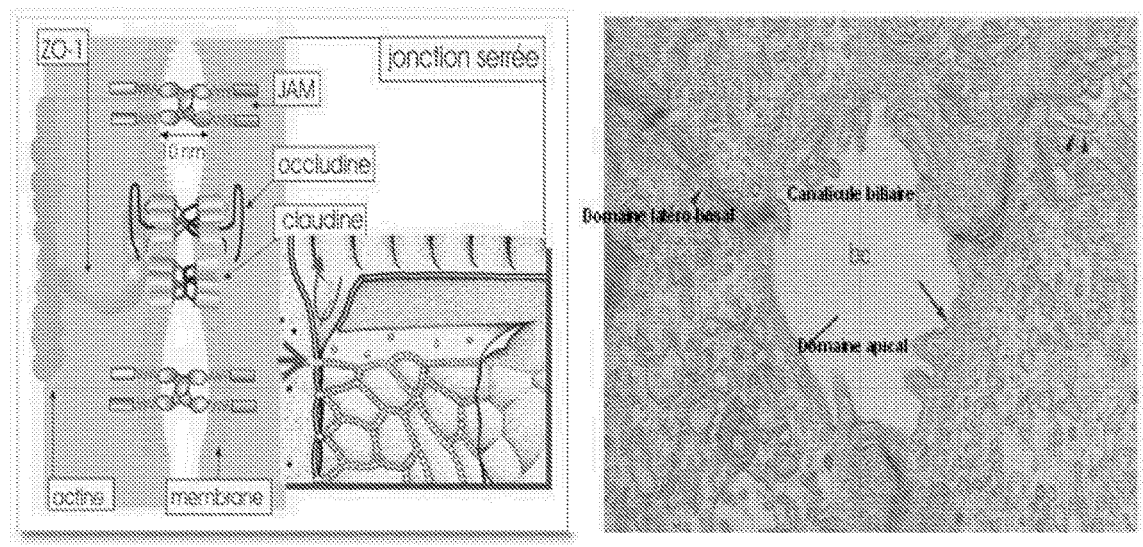
FIG. 2 is an illustration (left) and image (right) of the junctional complex around the canalicular lumen, and organization of tight junction and localization of junction proteins.

In one or more embodiments, there are disclosed processes related to modulating mechanical movement of bile canaliculi lumen through activation or inhibition of the Rho-kinase molecular regulation pathway. In one or more embodiments, there are disclosed processes related to modulating hepatic biliary polarity and differentiation through activation or inhibition of the Rho-kinase molecular regulation pathway. In one or more embodiments, there is disclosed an assay for screening a candidate compound (e.g., xenobiotic) for potential cholestatic side effects, and in particular for predicting a xenobiotic's effect on lumen contraction or swelling, such as the disappearance of the repeated coordinated movements and overall the loss of contraction/relaxation of the lumen needed for efflux and clearing the canaliculi lumen. In one or more embodiments, the xenobiotic activates Rho-kinase enzyme (such as chlorpromazine and cyclosporine A) and in consequence, favors the myosin II phosphorylation responsible for actin contraction. All effectors susceptible to generate free radicals are concerned. Indeed, free radicals, particularly NOs, are possible activators of Rho-kinase enzyme. In one or more embodiments, the xenobiotic inhibits Rho-kinase enzyme (such as bosentan) and in consequence reduces phosphorylated myosin II formation, resulting in actin relaxation. The xenobiotic can activate or inhibit directly the Rho-pathway or indirectly through other associated pathways such as endothelin or other growth factor pathways or calmodulin mediators. In another embodiment the invention includes the Rho-kinase-dependent activation or inhibition of myosin phosphorylation enzymes through MYPT-1, MLCP and MLCK enzymes, as well as all substrates of Rho-kinase and/or targeted enzymes (MYPT.1, MLCP and MLCK) such as eNOS and NO, L-glutamine, angiotensin II. Other targets in the pathway include phosphorylated myosin light chain (p-MLC), which plays a major role in controlling contraction and/or swelling of bile canalicular lumen.

In one embodiment the invention also includes the relationship between p-MLC, contraction and tight junction organization. It involves direct or indirect effects on constitutive tight junction proteins such as ZO-1, claudin and occludin, including their level of phosphorylation, reorganization of the cell layers at the apical ring and reorganization including positioning, of the junctional complex at the apical ring.

In one or more embodiments, there are disclosed processes related to modulating bile canaliculi/lumen opening and clearing using metalloproteinases (MMPs). In one or more embodiments, the MMPs contribute to changes of some junctional constitutive proteins such as ZO-1, claudin and occludin properties, mainly phosphorylation, leading to permeability of the junctional complex making possible the lumen opening and clearing. In one or more embodiments, the MMPs have the ability to modulate their activity levels (directly or indirectly) in response to transient and repeated contraction signaling occurring in normal canalicular structures, thus allowing regular opening and clearing of lumen pockets. The MMPs also contribute to permanent inhibition of perijunctional permeability resulting in alteration of lumen efflux activity in drug-induced cholestatic diseases. Further, MMP modulators such as inhibitors (e.g., TIMP1) are also involved in the regulation process as main MMP enzyme activation regulators.

The invention is particularly concerned with in vitro methods for evidencing and quantifying the drug-induced canalicular function disorders with bile canalicular clearing dysfunction. The basis of the invention is the correlation established between i) intracellular movements, mainly repeated contractile events of the apical canalicular domain supporting canaliculi lumen clearing and regular flow activity, ii) Rho-kinase activation or inhibition responsible for actin contraction or relaxation of the canalicular lumen, iii) and alteration of these events in presence of cholestatic drugs (xenobiotics). Therefore, this invention proposes a new method for characterizing and screening candidate compounds (xenobiotics) for susceptibility to interfere with these different events by setting a well-controlled, easy-to-use, integrated "Bile canalicular activity assay" which preferably includes determination of 3 main parameters:

Morphological changes of the bile canalicular space
Clearing efficiency of biliary components out of the canalicular space
Maximal accumulation of biliary components into the canalicular space In accordance with the present invention, a method is provided for characterizing alterations of cholestatic diseases and for the screening of candidate compounds or substrates with the potential to alter bile canaliculi function. In one or more embodiments, the method comprises providing an in vitro system with functional hepatic cells, in which the hepatic cell culture comprises at least one (and preferably numerous) bile canalicular structures easy to analyze and/or suitable to imaging. The culture is exposed to a candidate compound, which may include one or more compounds with the potential (or not) to induce biliary dysfunction. A Bile Canalicular Activity Assay, as described in more detail below, is then used to analyze the effect of the candidate compound on bile canaliculi activity. In general, the assay comprises detecting morphological alterations of the biliary space, administration of a marker compound to the culture, determination of a Canalicular Clearing Efficiency (CCE), and determination of the Maximal Biliary Components Accumulation (MBCA) in the canalicular space.

The hepatic cell culture is preferably an artificial, in vitro culture of viable cells, such as immortalized hepatocytes, primary cultured hepatocytes, freshly isolated hepatocytes, cryopreserved hepatocytes, sandwich-cultured hepatocytes. The culture can be configured as at least one layer of hepatic cells, or aggregates or 3-dimensional clusters of hepatocytes. The hepatocytes can be isolated from human and/or animal livers. Pooled hepatocyte cultures prepared from multiple sources may also be used. A cell "source," as used herein, refers cells obtained from various donors, biopsies, tissue resections from different tissue samples or different tissue sources, different animals harboring cells (species), or primary, secondary, immortalized, or transformed cells. The cells may be derived from any mammalian source, including human, porcine, simian, canine, feline, bovine, equine, ovine, leporine, or murine sources, among others, as well as avian sources.

As would be appreciated by one skill in the art, a cell model is selected that mimics the mechanical dynamics of hepatocytes in vivo, including intracellular trafficking of compounds mediated by strictly controlled cytoskeletal-dependent movements. Thus, the preferred hepatic culture for the present invention will contain morphologically normal hepatocytes, aggregated together by junctions in order to form at least one (and preferably a plurality of) morphologically normal (and functional) bile canalicular structures. The term "morphologically normal" refers to having the standard, usual, typical, or expected native/unaltered morphology. Preferably, hepatocytes will be functionally stable for long periods of time and demonstrated to preserve at a high rate, all main in vivo hepatic functions including the detoxification one. Preferably, the cells should evidence all characteristics associated with bile canalicular polarity and bile canalicular activity, comprising specific expression and localization of transporters. Additionally, the cell culture should evidence preserved control regulation of the junctional permeability responsible of the lumen space clearing and efficient efflux components release. Exemplary models thus, include hepatocytes in 2D or 3D systems, as primary cultures or prepared from engineered hepatic cell lines and able to undergo complete hepatocyte maturation process, including bile canalicular polarity organization and function. In accordance, HepaRG® (human hepatoma line deposit no. 1-2652, U.S. Pat. No. 7,456,018, incorporated by reference herein) or derivative or engineered cell lines thereof are preferred for use in the method of the present invention. The HepaRG® cell line is a model highly reproducible, producing human hepatocytes with long term stability, preferentially 14 days or more, and easy to use. In addition, these cells do not require embedding in a gel matrix, which can be susceptible to cause abnormal adsorption of compounds and/or limiting imaging applications. This does not preclude 3D and scaffolding configurations in the possible culture conditions used, if a scaffolding or a gel matrix were desired.

The term of "candidate compound" refers to any compound to be characterized for its potential to induce cholestatic effects, or otherwise disrupt biliary excretion. Accordingly, any compound susceptible to interfere with the trafficking machinery of the cells, comprising cytoskeletal movements and associated dynamic events coordinating exchange signaling from cells to cells and cells to microenvironment, permeability and barrier protection including permeability of junctional complex at the biliary pole could be considered a candidate compound. The candidate compounds screened in accordance with the method of the present invention include xenobiotics such as small molecule drugs, biologics, therapeutic agents, carcinogens and environmental pollutants, as well as all compounds prone to influence directly or indirectly, actin constriction and relaxation.

The culture is exposed to the candidate compound for a time sufficient to allow uptake by the hepatic cells and metabolism through detoxifying enzyme activity and/or fixation to transporters or other intracellular proteins. In accordance, time ranking and dose-responses kinetics are established. Preferentially but not exclusively, short term exposures will be used because of data showing early occurrence of the morphological changes of the biliary space.

In one or more embodiments, the method comprises determining alterations of the biliary space. This would involve determining (e.g., visually) morphological changes of the biliary space, including any changes of lumen size or shape using actin and/or apical transporters localization (such as pGP, BSEP, MRP2) and/or junctional proteins. Imaging quantification can provide mean size values for characterizing lumen constriction or swelling events. Thus, distinction between the two potential cholestatic phenotypes can be performed early, characterized by either constrained canalicular lumens or swollen canalicular lumens.

The method further comprises detecting (if any) evidence of canalicular clearance activity dysfunction associated with altered clearance efficiency of biliary components out of the canalicular space. In particular, the method comprises detecting and measuring a delay in canalicular lumen clearing function by quantifying movements of small molecules inside and/or outside the canalicular lumen. The method for bile canalicular activity measurement of the present invention involves the use of a "marker compound." This marker compound is preferably chosen for high throughput hepatic uptake and bile canalicular activity assay. This term refers to a chemical compound that can be readily detected using standard detection techniques, such as fluorescence or radio- and chemo-luminescence spectrometry, colorimetry, and the like. Exemplary markers used in the present invention include fluorescent compounds, but it does not exclude other known marker substrates. One embodiment of the invention is measurement of bile canalicular clearing activity and includes any alteration leading to biliary efflux alteration. Thus, the marker compound will be chosen for rapid penetration into the cells and efflux to the bile canaliculi, ease-of-use with high fluorescent properties and low interference with other cellular trafficking and movements. The preferred marker of the method of the present invention comprises the fluorescent MRP2 substrate, carboxychlorofluorescein, preferably carboxydichlorofluorescein diacetate which is a precursor rapidly and passively penetrating into the cells, hydrolyzed to a highly fluorescent product, and specifically transported to the biliary poles. Alternatively, other marker compounds include other transporter substrates such as mitotrackers, comprising rhodamine as shown in one laboratory example described below, or JC1 and others such as fluorescein-labelled taurocholate. Time ranking for getting appropriate fluorescence level is defined. Addition of a marker compound to the culture is performed in presence of the candidate compound or after candidate compound removal according to the inquiry being investigated.

In one or more embodiments, the presence of absence of a delay in canalicular lumen clearing can be assessed by establishing time-dependent kinetics of the marker compound, as it is directed to the apical domain of the cells and released from canalicular lumen to the culture medium to the apical domain of the cells. It can provide information onto the biliary clearance activity.

Canalicular clearance of the marker compound is qualitatively and quantitatively assessed in the method of the invention. In one or more embodiments, qualitative canalicular clearing activity measurement is performed by in situ time-lapse imaging approach. It shows a time-dependent disappearance of the intracanalicular marker compound due to gradual clearing from canaliculi and canalicular vesicles into the culture medium. Time-lapse is based on series of photos obtained from a microscope equipped for fluorescence at the right wavelength, from the same culture at increasing times of incubation, for example every 15 min during 1 hour. For example, as shown in the example below, there is a delay of clearance in the presence of chlorpromazine, a known cholestatic drug. Quantification of the delay can be performed by calculation of the Canalicular Clearance Efficiency (CCE) in treated cells and expressed as CCE per time unit. Optionally, comparison can be performed with control cells and a percentage can be calculated. The Canalicular Clearance Efficiency (CCE) calculation provides a percentage of accumulated marker compounds (e.g., fluorescent molecules) cleared out of the canaliculi and canalicular lumen per time unit. Susceptibility of candidate compounds to cholestatic side-effects can therefore be characterized by reduced CCE levels associated with lower percentages of released marker compounds into the culture medium compared to control cells. In other words, this indicates a loss of the mechanical movement needed for clearing of the lumen.

In one or more embodiments, the method further comprises evaluation of a complementary parameter, which directly links to both morphological changes of canalicular space and alteration of clearing activity. The inquiry uses calculation of Maximal Biliary Components Accumulation (MBCA) in the biliary reservoir space by exposing the culture to junctional space disruptors, these disruptors being chosen for specific permeabilization of canaliculi and canalicular vesicles, for rapid release of accumulated biliary components into the medium for quantification. The Maximal Biliary Components Accumulation (MBCA) defines the maximal amount of small (e.g., cell permeable, such as MW<~500 Daltons) or large molecules (typically cell-impermeable, MW>~500 Daltons) able to move either from the cell interior or from outside the cell to inside bile canaliculi and to accumulate into canaliculi and canalicular lumens. It is expressed as amount of marker compound accumulated into the canalicular space during a defined period (for example, 30 min. for small molecules, 20 h for large molecules).

Two complementary approaches are used to evaluate this:
The complete lumen clearance of small fluorescent dye molecules (marker compounds) such as fluorescent CDFDA addressed from the cell interior to the biliary pole and accumulated into the biliary reservoir space in control and drug-treated cells for a defined period of time; it is based onto the property of metalloproteinases such as activated MMP9 to specifically permeabilize the junction complex thus, allowing a rapid and highly reproducible release of accumulated fluorescent dye into the medium immediately suitable for quantification; and The entry of large fluorescent molecules such as BODIPY-C12-sphingomyelin unable to passively enter into the cell through basolateral domains and thus, to specifically entering from the cell exterior through—and accumulating in—the canalicular reservoir space.

Quantification of the Maximal Biliary Components Accumulated into the canalicular space is one main endpoint of the method of the invention. CDFDA is specifically directed to canalicular vesicles as described above, and the use of junctional disruptors permits the rapid and total clearing of the marker compound. This has an advantage over known assays, because it aims to avoid any change in the trafficking and cytoskeletal organization. Because Ca++-free treatment may deeply perturb several signaling pathways including that of Rho-kinase, the preferred junctional disruptors for the present invention belong to the metalloproteinases family (MMPs). These enzymes were recently described as playing a role on junctional complex, mainly on tight junctions. Advantageously in the scope of the invention, their major location in mature hepatocytes is at the bile canalicular membrane domain and their major role was reported to be alteration of junctional proteins and disruption/permeabilization of the junctional barrier.

Several MMPs can play this role, including MMP2, MMP7, MMP9 and others. These MMPs are preferably in an inactive form. Therefore, before use activation of MMPs is requested. Preferably, activation is obtained by incubation with p-aminophenylmercuric acetate (APMA) overnight at 37° C. (Vermeer P D et al., 2009). Then, addition of MMPs to the culture can take place just before addition of the marker compound or concomitantly with the marker compound or after the marker compound accumulation depending upon the type of inquiry. Exemplary MMPs to be used in the invention, include MMP9, as well as any other MMPs such as MMP2.

This assay allows quantifying the maximal biliary components accumulation in the biliary space (mBCA). This quantification relies to "the biliary space." This term refers to the total surface internal to the canalicular network including the narrow surfaces of canaliculi and larger surfaces as a way to approximate the volume of the canalicular lumens. Preferentially, the mBCA will be calculated from differentiated hepatic cells exposed to the candidate compounds (for 2-4 hrs accordingly), then washed and exposed to the marker compound for dye accumulation into biliary space (around 30 min according to the dye), then washed and permeabilized with activated MMPs, preferentially MMP9 (around 45-60 min) for complete dye molecules release into the medium followed by immediate fluorescence quantification, for example, in the supernatant.

Optionally, permeabilization of junctions with metalloproteinases can be performed during large fluorescent molecules entry in order to favour it. This latter test allows controlling the efficacy of metalloproteinase permeabilization in the assay. It also allows the verification of junctional space permeability after MMP treatment. Preferably, large fluorescent molecules belonging to the BODIPY family, such as BODYPY-C12-sphingomyelin, could be used. Those molecules cannot move inside the cells except throughout the canalicular space, and permeabilization with MMPs greatly potentiates dye entry. Because of the large molecules size of the dye marker compound, maximal accumulation is obtained after several hours so that the order of steps is different. Preferentially, differentiated cells are exposed to the candidate compounds as above, then cells are washed and exposed simultaneously to the large size marker molecules and to activated MMP (around 45-60 min), or the large size marker compound is exposed to the cell culture after exposure to the MMP, then washed and incubated for dye accumulation in culture medium (around 20 h after addition), then disrupted with Triton X100 solution for complete dye release into the medium and fluorescence quantification.

The invention also contemplates complementary assays, including detection of myosin light chain accumulated in its phosphorylated form using in situ immunolocalization or western blotting analytical strategies. It will provide a signature of abnormal Rho-kinase pathway activity. Commercially available kits can also be used to measure Rho-kinase activity based on quantification of accumulated phosphorylated myosin II form responsible for actin contraction (kit distributed by Merck-Millipore). In addition, imaging analyses using HCS or time-lapse strategies can be adapted for efficient screening.

The term of "detection of biliary lumen and/or junctional disorders" refers to any changes in lumen size or shape, actin constriction or relaxation, junctional protein expression and distribution in the junctional complex, MMPs expression/activation and membrane or intracellular localization. Preferably, F-actin organization around the pericanalicular ring is assessed using phalloidin staining. However, actin distribution is not limited to the apical pole, advantageously all fluorescent marker compounds driven to the biliary pole by transporters can be used as well for High Content Screening with imaging analysis. Exemplary assay was performed using CDFDA as marker compound. Additional tools such as immunostaining can be selected for specifically localizing specific apical transporters, specific junctional proteins, MMPs or p-Myosin light chain.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

To the extent the present description uses numerical ranges to quantify certain parameters relating to various embodiments of the invention, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention. The following Laboratory Examples pertain to the establishment of a correlation of altered biliary clearance activity with morphological and mechanical disorders of bile canaliculi.

Introduction

It is well established that morphogenesis dynamics participating in the occurrence of bile canalicular lumens and contributing to their polarized organization in hepatocytes, involve signaling cascades driving the apical surface-directed membrane trafficking that are highly controlled. The main players in these controls include Rab proteins, Rho GTPases (including Rho-kinase) and actin distribution for cytoskeleton organization and cell motility. Rho-kinase pathway has been reported contributing to the establishment of apical polarity in liver cells. However, its contribution to the canalicular lumen function and to the bile salt flow and drug clearance as well, has never been studied and is not recognized.

Figure 3:
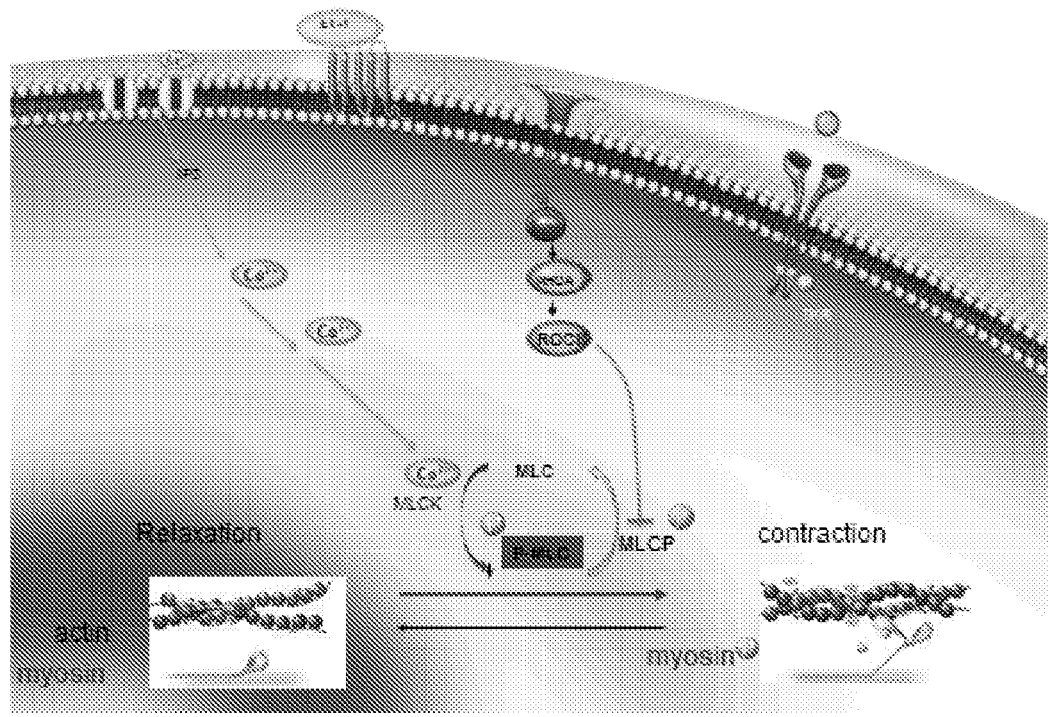
FIG. 3 is a schematic representation of the Rho-kinase pathway.

The role of Rho-kinase pathway (FIG. 3) in vasocontraction and the regulation of vascular tone has been documented, along with the Rho-kinase pathway activation fate as a critical event for contraction of vascular smooth muscle. For instance, specific therapy for pulmonary arterial hypertension (PAH) in sight was claimed from the last 5 years through several convincing experimental studies demonstrating that novel candidate drugs for the treatment of PAH are superior to two of the most potent anti-PAH drugs currently available. The therapeutic strategy involved inhibition of the enzyme, Rho-kinase, which was believed to play a key role in the pathogenesis of the disease. Indeed, the first step of this pathway activation involves contractile agonists through G-protein coupled vasopressor receptors. Then, these receptors activate the small monomeric GTPase, RhoA. Thereafter, RhoA activates Rho-kinase, which subsequently inhibits the myosin-light-chain-phosphatase (MLC-phosphatase) thus, resulting in enhanced accumulation of phosphorylated myosin II that interacts with actin for inducing contraction reaction. However, most drugs based onto Rho-kinase inhibitor therapeutic concept, appear susceptible to develop cholestatic side effects. Bosentan and Fasudil can be considered as main representative candidates in the list.

How can vascular vasopressor receptor inhibitors be associated with cholestatic machinery? Rho-kinase has been shown to mediate regulation of the intrahepatic vascular tone in human cirrhotic liver and in rats with bile ductular ligation. However, a direct contribution of the Rho-kinase pathway in occurrence of intrahepatic disorders associated with alteration of bile canalicular activity has never been demonstrated with these drugs.

Actomyosin complex activation responsible for the contraction of the apical ring of epithelial layers is mediated by Rho-kinase-dependent myosin light chain phosphorylation. In contrast, the mechanism controlling the opening of physical barriers formed by the apical junction complexes at the apical domain for lumen pocket clearing, remains questionable. Various studies have been previously performed using epithelial cell models such as Caco 2 and MDCKII. However, polarized hepatocytes were never analysed in this context and the concept involving bile canalicular lumen contractility in association with myosin phosphorylation was never considered or recognized.

The formation and maintenance of these barriers are dependent on a series of cell-cell contacts that circumscribe the apical-lateral margin of each cell which involve the adherens junctions (AJ) that promote strong adhesive interfaces between individual cells, and the tight junctions (TJ), which form a physical barrier to the movement between cells of ions, macromolecules, immune cells, and pathogens. Both AJ and TJ are intimately associated with the cortical actin cytoskeleton and are functionally regulated by circumferential actomyosin filaments.

At the molecular level, involvement of junctional constitutive proteins such as ZO proteins, in apical constriction was shown. Thus, experimental knockdown of these ZO proteins in MDCKII cells has been shown to cause a redistribution of markers commonly associated with the activation of actomyosin contraction such as ROCK-1, total MLC, or 1p-MLC without altering protein levels. In fact, in these studies, little if any 1p-MLC in the AJC was detected in normal cells.

In summary, myosin light chain phosphorylation contributes to the activation of actomyosin constriction and appears to modulate tight junction organization through involvement of constitutive proteins like ZO-1, claudin and occludin proteins, thus controlling to some extent the permeability of paracellular spaces of epithelial apical rings for small molecules. Regarding large molecules one model is proposed that they could pass through transient breaks, and permeability over time would be the sum of movements across several breaks in series. It has been proposed that contraction of the peri-junctional actomyosin ring might cause such transient breaks.

Figure 4:
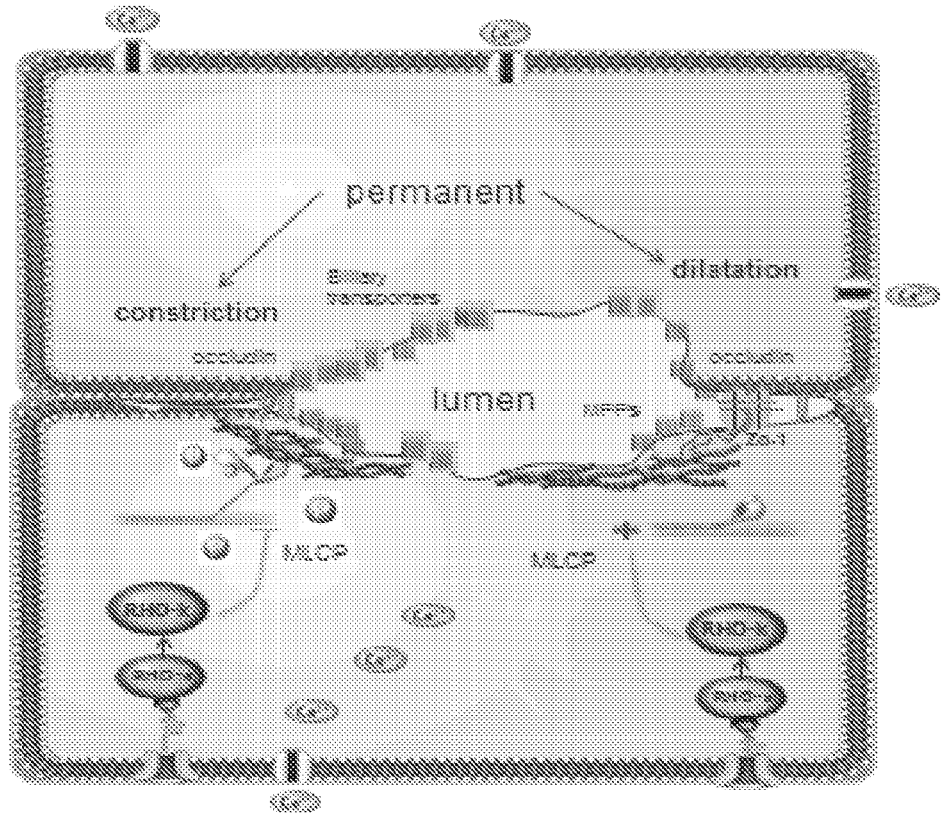
FIG. 4 is a schematic representation of the bile canalicular space with all of the main regulating factors to illustrate the mechanical control of abnormal junctional complex permeability.

Other important partners of this contraction control could be represented by the metalloproteinase enzymes family. The role of these enzymes has been limited to controlling the extracellular matrix deposition and organization. However, during the last ten years, they have been described as playing many other functions such as a direct role onto myosin light chain degradation and onto proteins forming the actomyosin ring. Interestingly, metalloproteinase MMP2 was recently shown to be able to modulate abnormal contractile activity in heart failure situations. MMP2, 3, 7, 9 are highly expressed and mainly localized at the apical domain of bile canaliculi, i.e., close to junctional complexes (FIG. 4). Their role on canalicular junctional barrier permeability is not established and nothing is known on MMPs and their role on permeability of bile canalicular lumens into the liver.

Example 1

Comparison of progenitors and differentiated HepaRG cells to primary human hepatocyte monolayers (HH) sandwiched collagen layers (S-HH). The cells were treated with CPZ and different cholestatic drugs, with control of RHO-kinase Pathway by activators and inhibitors: ROCKi (Y27632) and myosin heavy chain ATPase inhibitor (BDM). Immunofluorescence and imaging analysis was conducted for cell polarity description. Uptake and release of bile acid taurocholate for canalicular efflux measurement was performed. RHO-kinase pathway induction or inhibition was analyzed.

1 Apical Bile Canaliculi Formation
1.1 Occurrence of Canalicular Polarity in HepaRG Cells Versus Human Hepatocytes Cell Cultures. HepaRG cells were seeded at a density of 300 000 cells/well from 24 well-plates in Williams E medium supplemented with 10% fetal bovine serum, 100 U/mL penicillin, 100 mg/mL streptomycin, 5 mg/mL insulin, 2 mM glutamine, and 50 mM hydrocortisone hemisuccinate. After 1 week, HepaRG cells were shifted to the same medium supplemented with 1.7% dimethyl sulfoxide for a further 2 weeks in order to obtain confluent differentiated cultures with maximum functional activities. At this time, these cultures contained mature hepatocyte-like cells surrounded by primitive biliary cells.

1.2 Determination of Cell Polarity

Figure 5:
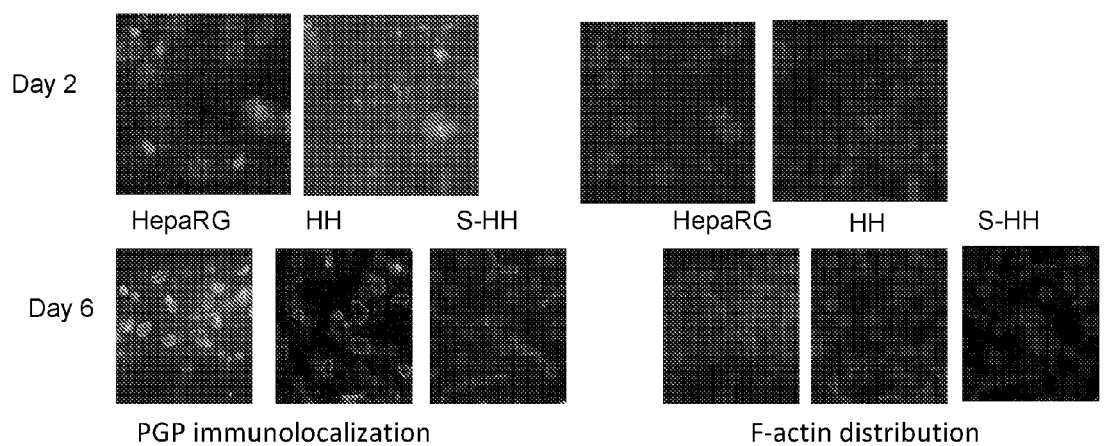
FIG. 5 shows immunofluorescence and imaging analysis of canalicular polarity polarity in HepaRG cells as compared to primary human hepatocytes.
Figure 6:
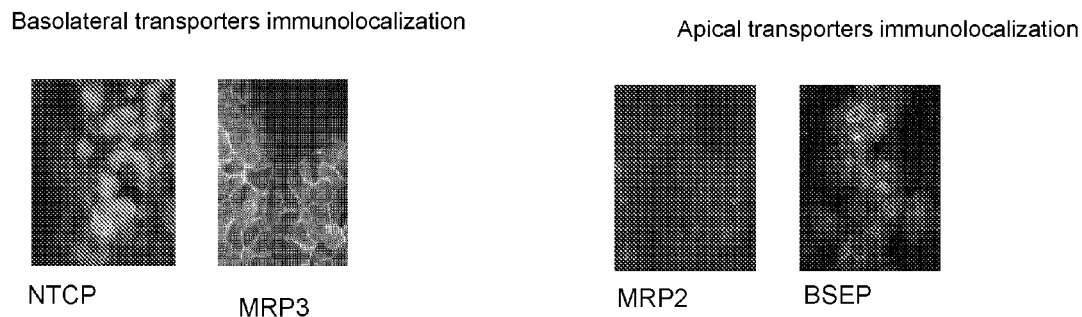
FIG. 6 imaging of immunolocalization of basolateral and apical transporters.

HepaRG cells were chosen at different times during the differentiation process: day 2 corresponding to early progenitors, and day 6 corresponding to later progenitors. Bile canaliculi were detected by dense F-actin lining bile canalicular lumen. For staining F-actin, transporter proteins pGP, MRP2 and MRP3, and junctional protein ZO-1, cells were fixed in 4% paraformaldehyde (wt:vol in MSS; pH 7.2) for 20 min. After washing 3 times, cells were permeabilized with 0.1% Triton X-100 (wt/vol in HBSS for 5 min at room temperature. Cells were washed and blocked with 1% BSA (wt/vol in MSS; pH 7.4) for 30 min at room temperature. BSA was removed and cells were incubated with the first mAb at room temperature. Cells were washed and incubated with the secondary antibodies (2 µg/ml) conjugated with Alexa-fluor-488 or 596 (diluted 1/400 in MSS) for 45 min at room temperature. Cells were washed and observed with microscope Zeiss. Optionally, cells were counterstained with Hoechst solution. See FIG. 5 and FIG. 6

1.3 Canalicular Polarity Controlled by Rho-Kinase Pathway

Figure 7:
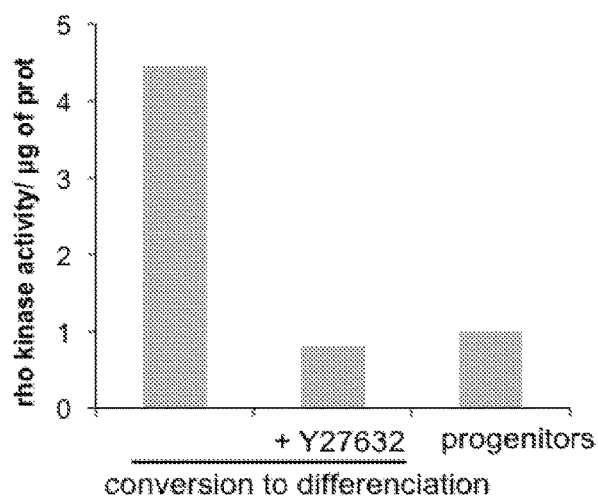
FIG. 7 is a graph showing the polarity is controlled by the Rho-kinase pathway.

Cells were cultured as described above. Two days after seeding, undifferentiated progenitors were cultured in the absence or presence of the specific ROCK inhibitor Y27632 (2.5 µM) and daily observed for differentiation progression. In parallel, Rho-kinase activity was measured using a Rho-kinase kit (Merk-Millipore) according to the manufacturer. See FIG. 7. Bile canaliculi lumen distribution is identical in differentiated HepaRG and primary human hepatocytes at Day 6. Rho-kinase contributes to establish apical polarity in both models.

Figure 8:
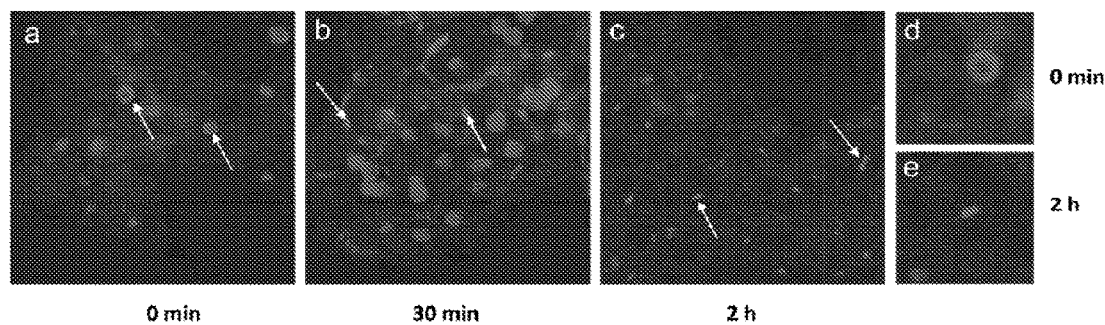
FIG. 8 is imaging showing constriction of the canaliculus lumen after exposure to chlorpromazine.

2—CPZ Induced Constriction of Canaliculi Inhibited by Rho-Kinase Inhibitor
2.1 Induction of Constriction by CPZ in HepaRG Cells Two week DMSO-treated HepaRG cultures were exposed to 50 µM CPZ for 2 h and analyzed at different times during exposure. Constriction was evidenced by F-actin staining using phalloidin. See FIG. 8.

2.2 Modification of Efflux by CPZ in HepaRG Cells

Figure 9:
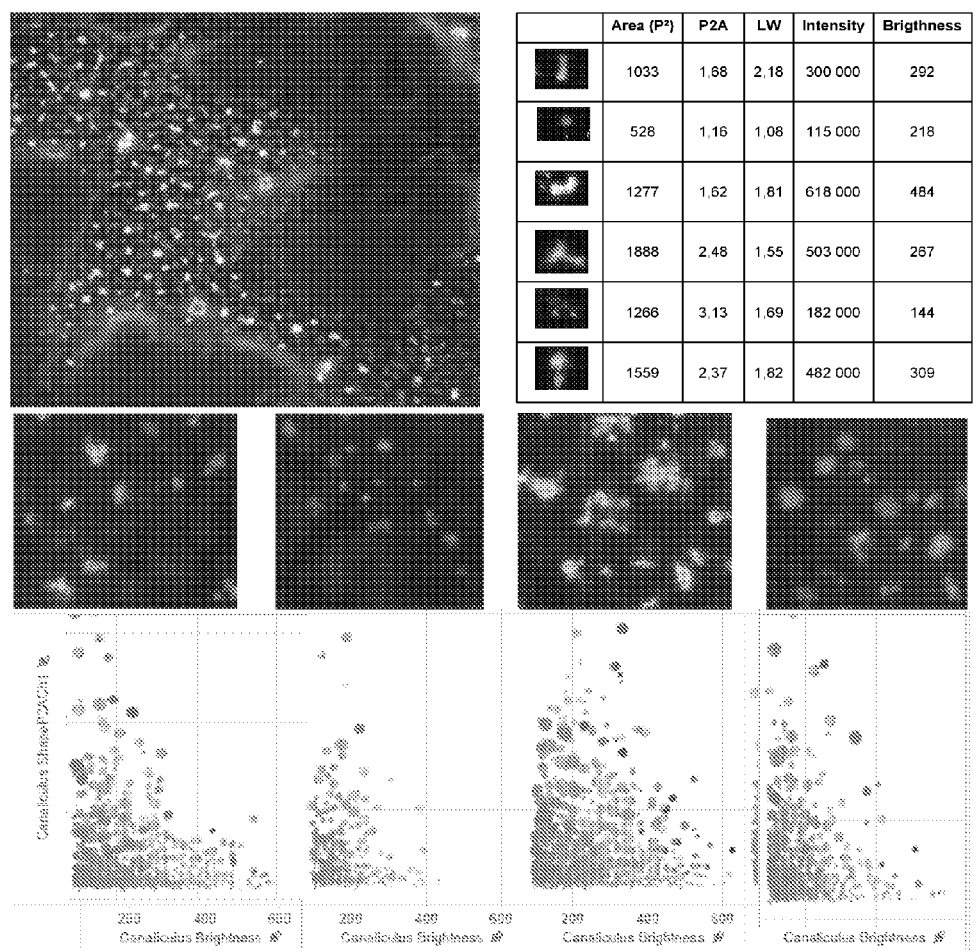
FIG. 9 shows imaging analysis of the bile canaliculi.

Efflux of Taurocholate (TA). Cells were first exposed to [3H]-TA for 30 min, then washed with PBS and incubated with or without CPZ at different time points (from 0 to 6 hours) in a standard buffer with Ca2+ and Mg2+. After the incubation time, cells were washed with PBS and incubated for 5 min with a Ca2+ and Mg2+– free buffer in order to disrupt the canalicular tight junctions. Then they were scraped in 0.1 N NaOH; the remaining radiolabeled substrate was measured through scintillation counting to determinate TA efflux. To discriminate between basolateral and canalicular efflux, cells were incubated in parallel in either standard or Ca2+ and Mg2+-free buffer for 30 minutes after TA uptake before measuring the remaining radiolabeled TA. Canalicular efflux was calculated using this equation: Canalicular efflux: Radioactivity in efflux mediumCa2+ and Mg2+ free buffer—Radioactivity in efflux medium Standard buffer. Differentiated cells were exposed or not to CPZ (50 µM for 2 h) before radiolabelled TA addition. See FIG. 9.

2.3 Cytoskeleton Reorganization

Figure 10:
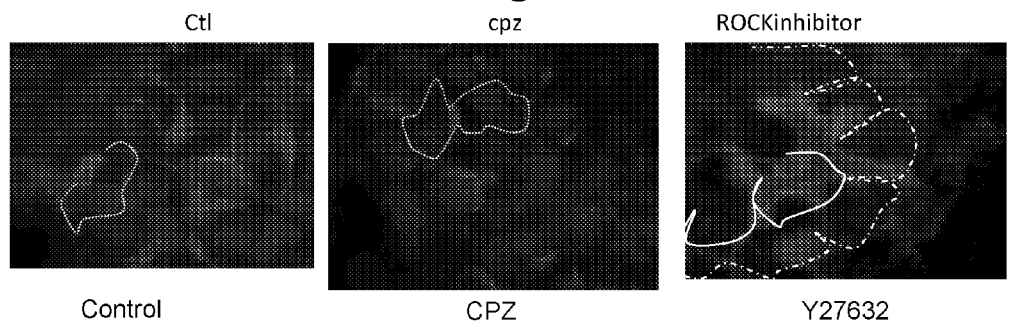
FIG. 10 shows imaging demonstrating cytoskeletal reorganization in the presence of a Rho-kinase activator chlorpromazine (constriction) or a Rho-kinase inhibitor Y27632 (swelling/relaxation)

Comparison of the cytoskeleton organization of control cells versus CPZ and Y27632 treated cultures for 2 h. Fibers of F-actin accumulated at the biliary were labelling by phalloidin and counterstaining of nuclei was performed by Hoechst staining. See FIG. 10.

Constriction of canaliculus lumen has been observed in the presence of CPZ after 2 hours. Reorganization of cells forming the biliary lumen according to the construction (CPZ) or swelling (Y27632) events induced by the drugs. Change of morphology correlated with a loss of bile canaliculi activity, with a decrease of taurocholate efflux in presence of CPZ. The presence of RHOKi with CPZ induces the recovery of taurocholate efflux activity.

In summary, constriction of the canalicular lumen or swelling in presence of Rho-kinase inhibitor, are associated with reorganization of the cell monolayer and reorganization of intracellular cytoskeleton which result in altering the normal movements of the cells and mainly that leading to clear the lumen pocket.

3—ROCK Activation Mimics CPZ-Induced Constriction 3.1 Involvement of Rho-Kinase Pathway Differentiated HepaRG cells were exposed to increased doses of CPZ (from 1-50 μM) for 2 h and Rho-kinase activity was measured (kit Merck-Millipore) according to manufacturer. Untreated cells and cells exposed to the Rho-kinase inhibitor Y27632 (10 μM) were used for controls.

Figure 11:
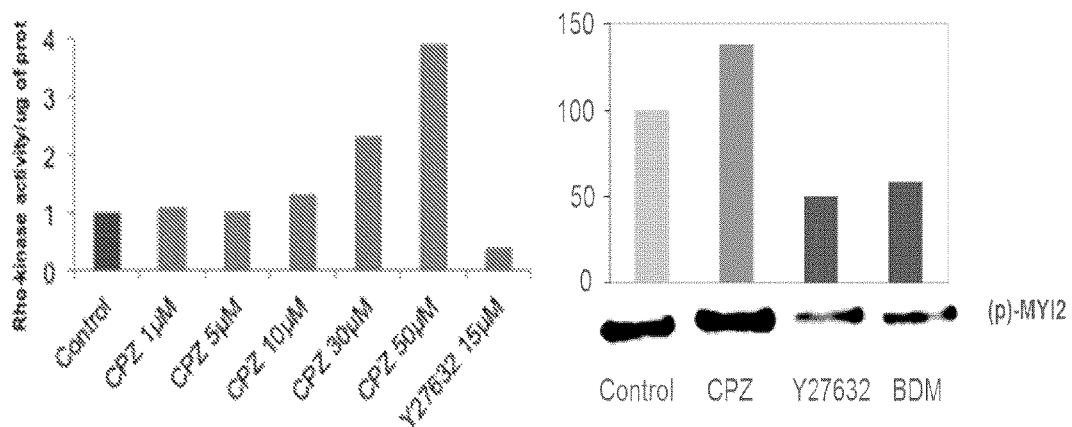
FIG. 11 shows a graph demonstrating the involvement of the Rho-kinase pathway with various cholestatic agents.
Figure 12:
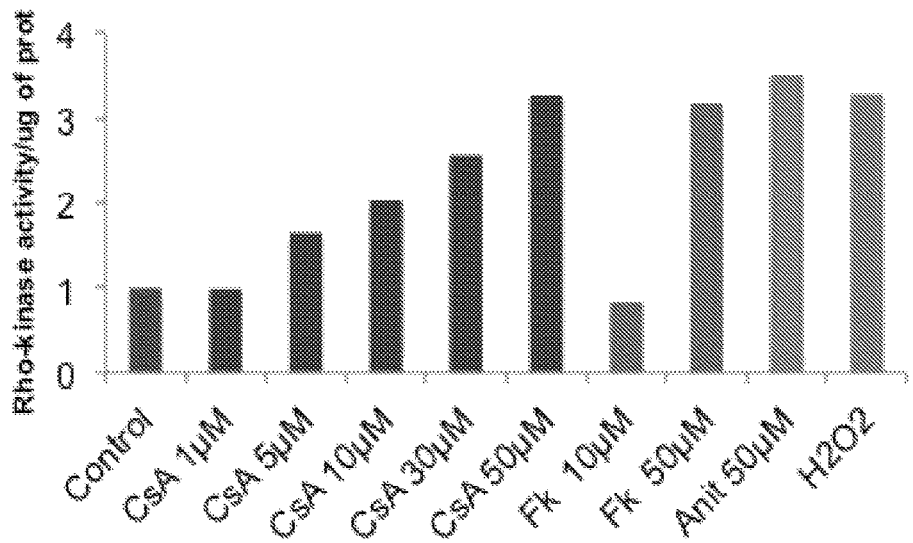
FIG. 12 is a graph demonstrating that other cholestatic agents require activation of the Rho-kinase pathway.

Accumulation of phosphorylated light chain myosin was evidenced by western blotting technique in using the (P)-MY12 antibody. Control cells, 2h-CPZ treated cells and 2h-y27632-treated cells were compared. Cell lysates were prepared. See FIG. 11. A dose-dependent activation of Rho-kinase is observed with CPZ and activation is associated with accumulation of myosin-light chain phosphorylation as shown by immunoblotting with antibody specific of phosphorylated myosin (p-MY12); Y27632: Rho-kinase inhibitor; BDM: myosin phosphorylation inhibitor 3.2 Other Cholestatic Agents Require Rho-Kinase Pathway Activation Control differentiated HepaRG cultures and cultures were treated with increasing concentrations of Cyclosporin A (From 1-50 μM) and Tacrolimus (1 and 50 μM) for 2 h, then harvested and lysates were prepared as above and used for Rho-kinase activity. See FIG. 12. These cholestatic agents are all inducing lumen constriction. CsA: Cyclosporin A; Fk: Tacrolimus; Anit are all known to induce cholestatic effects. They activate the Rho-kinase activity.

Example 2

Material and Methods Used in the Example

Cell Lines and Cell Cultures.

Subconfluent HepaRG cells from passages 12 to 16, were detached by trypsin-EDTA solution for 5 min, and reseeded at density of 300 000 cells per well of 24 well-plates, in William's E medium containing hydrocortisone hemysuccinate (10-6 M), insulin (4 μg/ml) and 10% FCF as previously described (Gripon Petal; 2002; Pernelle K., 2011). They were maintained for 1 week and got confluence. At this stage they have committed to hepatocyte differentiation. They were maintained for 2 additional weeks in the same medium added with 1.7% DMSO. DMSO allowed the cells to complete their maturation program. Mature cells were used after 2 weeks exposure to DMSO for candidate compounds testing. Medium was renewed three times per week.

Exposure to Candidate Compounds.

The candidate compounds were cholestatic drugs such as chlorpromazine, cyclosporine B and Effectin or Fasudil. Compounds were solved in water or DMSO according to the supplier recommendations. For demonstration, chlorpromazine (CPZ) was used at 50 μM, a sub-toxic dose for 1 to 4 hours exposure (Antherieu S., 2013). Antagonist molecules to Rho-kinase such as Y27632 also named Effectin (EF) were used as negative controls. For demonstration, EF was used at 10 μM after dilution in water and kept in at −20° C.

Two-week-old differentiated HepaRG cell cultures were washed once with fresh medium and exposed to candidate compounds added to the medium at the concentration as above or at increasing concentrations in order to establish dose-response kinetics. Exposure lasted from 30 min to 4 h, according to the experiment.

Detection of Mechanical Disorder in Cell Movements with Modification of the Biliary Space.

Two complementary approaches have been performed:

i)—Analysis of the mechanical movements of control and treated cells by time-lapse, making possible to observe living cells in situ under phase contrast using microscope (AxioVision, Zeiss). Three films were built with series of images collected from over 4 h observation period, corresponding to control cells and cells treated with CPZ and with EF; and ii)—Analysis of the F-actin organization and biliary lumen changes using phalloidin and fluorescent CDFDA staining. After exposure to the candidate compounds, cells were washed twice, fixed with Paraformaldehyde (4%) fixative for 20 min, washed and stained with phalloidin for 10 min. For CDFDA staining, details are provided below.

Images obtained on microscope were used for calculating the size of the biliary lumen after treatment. Appropriate algorithm has been developed for quantification using Cellomics equipment. Constriction was detected in presence of CPZ whereas swelling was observed with EF.

Analysis of transporters (pGP, MRP2, etc.), junctional proteins (ZO-1, claudin and occludin) has been performed by immunolocalization using specific antibodies. Accumulation of the phosphorylated myosin light chain was performed by western blotting using p-Myl antibody.

Biliary Clearance Activity.

The first step was incubation with the marker compound. CDFDA was preferentially used. After washing, differentiated cells plated in wells from 24 well-plates, were washed with HBSS buffer twice and incubated with 250 μl of CDFDA solution prepared at the final concentration of 3 μM in HBSS buffer containing Ca++ buffer (pH 7.4). After 30 min cells were washed with the same buffer. The kinetics of CDFDA clearing out of the canalicular space was followed by imaging every 15 min for 1 h, showing the gradual disappearance of the fluorescent dye, using a microscope equipped for fluorescence staining at the wavelength between 390 and 420. Quantification of the fluorescent dye into the medium is performed.

A comparative evolution was established between control (untreated) and CPZ- and EF-treated cells. A delay in the clearance of dye was clearly observed. Calculation of the amount of released fluorescent dye molecules was performed by spectrometry and the canalicular clearance efficiency (CCE) was determined per time unit.

Another assay was performed with Rhodamin 123 as marker compound. A delay was also observed in dye clearance with both CPZ and EF candidate compounds, thus confirming the possibility to use another marker compound for the test. We notice as expected, the background of intracellular red fluorescence which was maintained due to mitochondrial labelling with the dye.

Maximal Biliary Components Accumulation in the Biliary Space.

This last step of the Biliary Activity Assay involves incubation with the marker compound and CDFDA was preferentially used as above. After 30 min cells were washed with the same HBSS buffer. Then permeabilization of the junctional space with metalloproteinases is performed for 30 min. MMP9 was preferentially used. A stock solution was prepared at 10 mM in a Tris buffer. Activation of MMP9 was requested as described by Vermeer P D et al. (2009). Activation was performed by incubation with p-aminophenylmercuric acetate (APMA) overnight at 37° C. (for 20 h). APMA solution was solved in DMSO and used at a concentration of 10 mM. It was diluted 10 times by mixing with MMP9 solution in order to get a final APMA concentration of 1 mM. Activated MMP9 solution was used immediately after activation at a final concentration of 0.54 µM into the medium. Cells untreated or treated with candidate compounds and then, incubated with the marker compound (CDFDA in our assay) for 30 min, were washed twice with HBSS buffer containing Ca++, and immediately incubated with the activated MMP9 solution for 30 min. Release of the fluorescent marker to the medium was followed by observation every 15 min. The dye release was very rapid in presence of MMP9 compared to MMP9 negative wells, indicating efficacy of the enzyme treatment. Quantification of the released dye into the medium by spectrometry allows determination of the maximal Biliary Components Accumulation (mBCA) per $10^6$ cells/per time unit.

The Sphingomyelin-BODIPY Assay:

An alternative to the mBCA calculation was performed using BODIPY-C12-sphingomyelin as marker compound. This marker was prepared as describes by Vermeer P D et al. (2009). BODIPY-FL-C12-sphingo-myelin (Invitrogen-Molecular Probes, Carlsbad, Calif.) was incubated with 10 mg of BSA in P buffer (145 mM NaCl, 10 mM HEPES, pH7.4, 1 mM Na pyruvate, 10 mM glucose, 3 mM CaCl2) for 30 min on ice to generate sphingomyelin-BODIPY-BSA. Differentiated HepaRG cells were washed with chilled P-buffer three times. Sphingomyelin-BODIPY-BSA was applied to the cells for 10-15 min after which it was aspirated and cells were washed twice with ice-cold P buffer. Cells were maintained on ice for 1 h and then analyzed on microscope. For defined experiments cells were treated with activated MMP9 at 37° C. for 30 min just before sphingomyelin-BODIPY addition. Calculation of mBCA can be performed by breaking the cells with a Triton X-100 solution and analysis of the fluorescence into the medium.

Results

Figure 13:
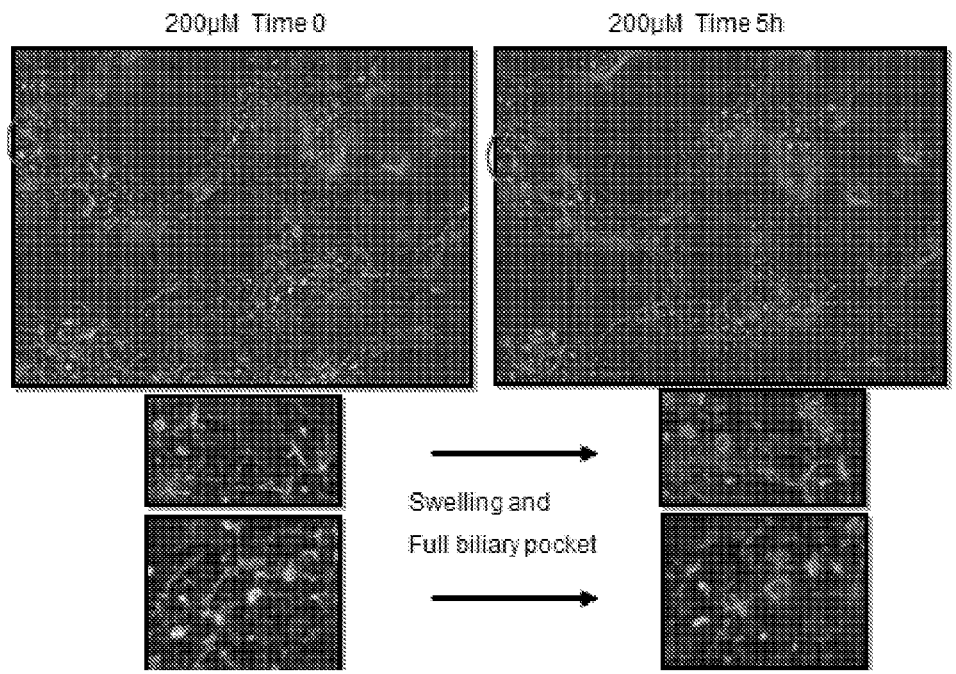
FIG. 13 is shows imaging for a new cholestatic phenotype of a swollen lumen, where the drug family of endothelin receptor antagonists (ERAs) also induce cholestasis through relaxation and swelling.

The results indicate evidence of two distinct cholestatic phenotypes. Example 1 demonstrates a cholestatic phenotype with lumen constriction. Example 2 demonstrates a new cholestatic phenotype with swollen lumen. As shown in FIG. 13, the drug family of endothelin receptor antagonists (ERAs) also induces cholestasis. Other examples inducing cholestasis are Rho-kinase Inhibitors such as Fasudil, ANIT and Deoxycholic acid (DCA).

Figure 14:
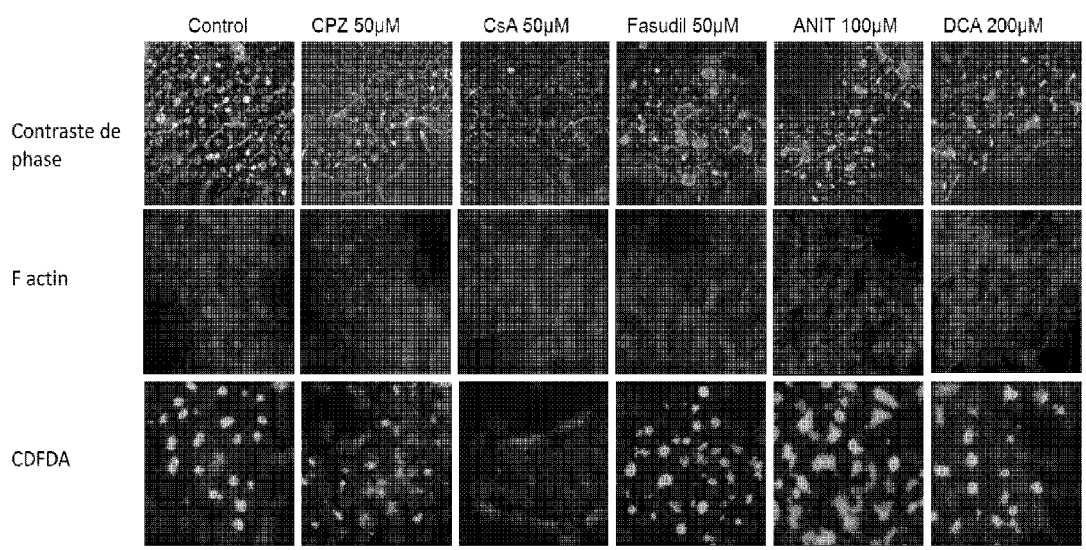
FIG. 14 shows imaging of hepatic cells modulated using chlorpromazine or cyclosporine A (constriction) or Fasudil, ANIT, or SCA (relaxation/swelling), and F-actin labeled with phalloidin, nuclei with Hoechst staining, and fluorescent marker compound (CDFDA) which accumulates in the biliary lumen.

The results also demonstrate an alteration of canalicular space using F-actin labelling. FIG. 14 shows lumen constriction with CPZ and CsA and swelling with Fasudil, ANIT and SCA. Living cells observed by phase contrast don't suffer from toxicity. F-actin is labelled with phalloidin; Nuclei with Hoechst staining. As can be seen, the fluorescent CDFDA compound accumulates in the biliary lumen.

Figure 15:
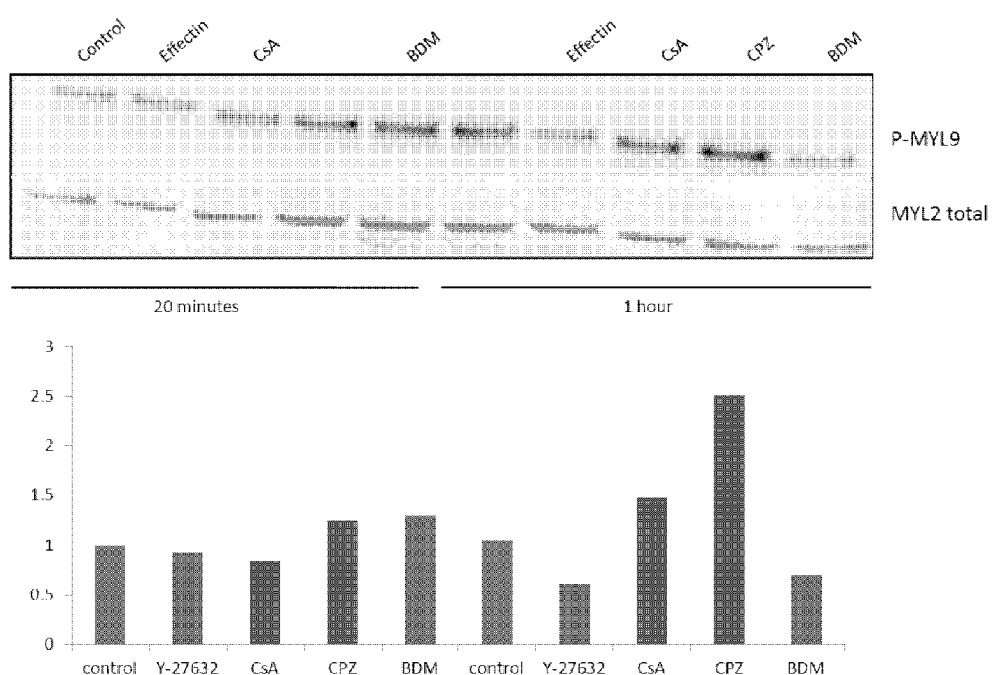
FIG. 15 shows a Western Blot (top) using antibodies against the total myosin and the specific phosphorylated form P-MYL9, and a histogram (bottom) representing the relative amounts of P-MYL9.

The results also indicate a direct contribution of the Rho-kinase pathway in the canalicular constriction/relaxation. This can be seen from Example 1. Further, as shown in Example 2 and FIG. 15, there is an accumulation of P-myosin in the presence of Rho-kinase activators (CPZ and CsA) and an inhibition of P-myosin phosphorylation in the presence of Rho-kinase inhibitors (Effectin, and BDM) after 1 hour. Western blotting using antibodies against the total myosin and the specific phosphorylated form P-MYL9 is also shown. The histogram represents the relative amounts of P-MYL9.

Figure 16:
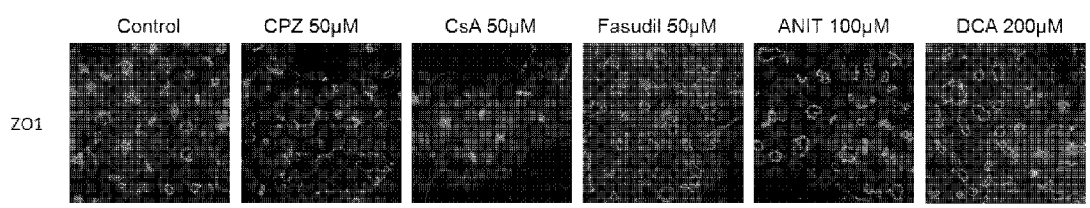
FIG. 16 shows imaging of cells for expression and distribution of a junctional protein in cells treated with inhibitors or activators of Rho-kinase.
Figure 17:
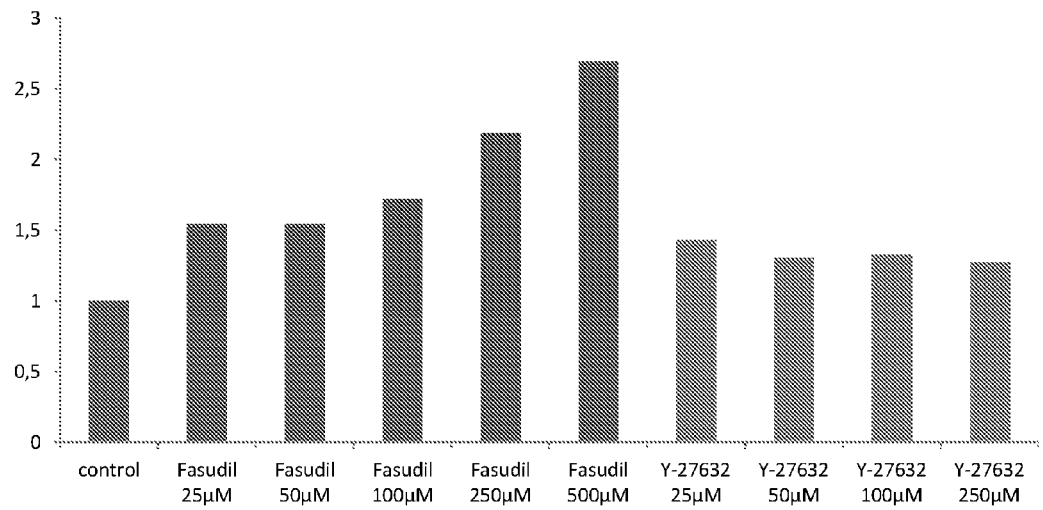
FIG. 17 is a graph of quantification of labelled taucholate accumulated in the cells (including the canalicular space) as a function of increased concentrations of Rho-kinase inhibitors (fasudil and Y27632)

The data also provides information related to junctional complex organization and the role of metalloproteinases in controlling permeability. FIG. 16 shows expression and distribution of one junctional protein, ZO-1 in cell cultures treated with Rho-kinase activators (CPZ and CsA) and inhibitors (fasudil, Anit and DCA, using a specific first antibody. Note that in all cultures the distribution of the protein at the biliary pole appears normal. In contrast, we found an abnormal accumulation of labelled taurocholate in presence of the Rho-kinase inhibitors Fasudil and Y27632. FIG. 17 shows quantification of labelled taucholate accumulated into the cells including the canaliculi space, as a function of increased concentrations of fasudil and Y27632 compounds compared to the control condition. Note the highest values with fasudil which is responsible for numerous swollen lumens.

Figure 18:
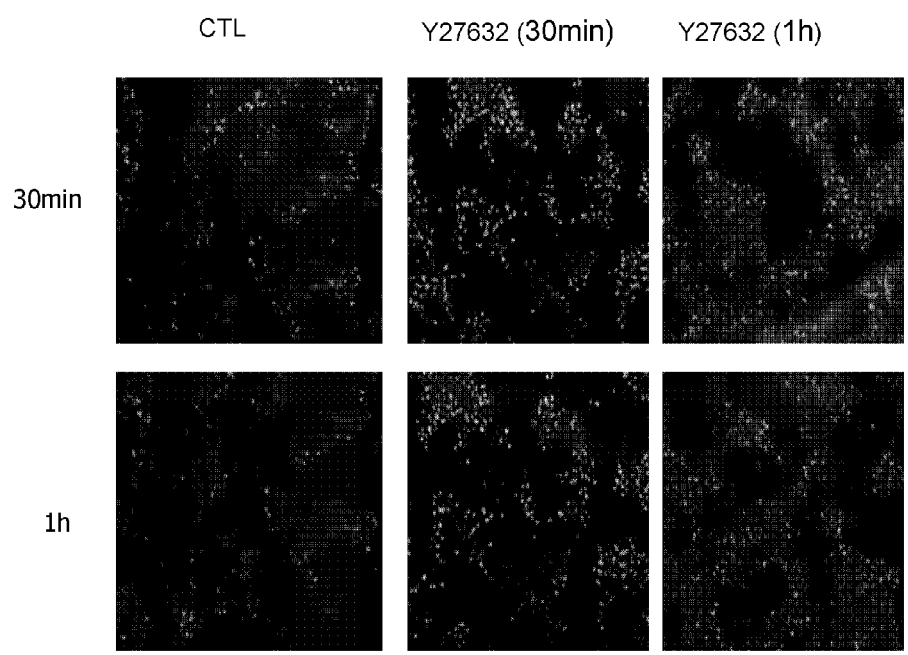
FIG. 18 is fluorescent imaging of cells exposed to a Rho-kinase inhibitor in the presence of a marker compound.
Figure 19:
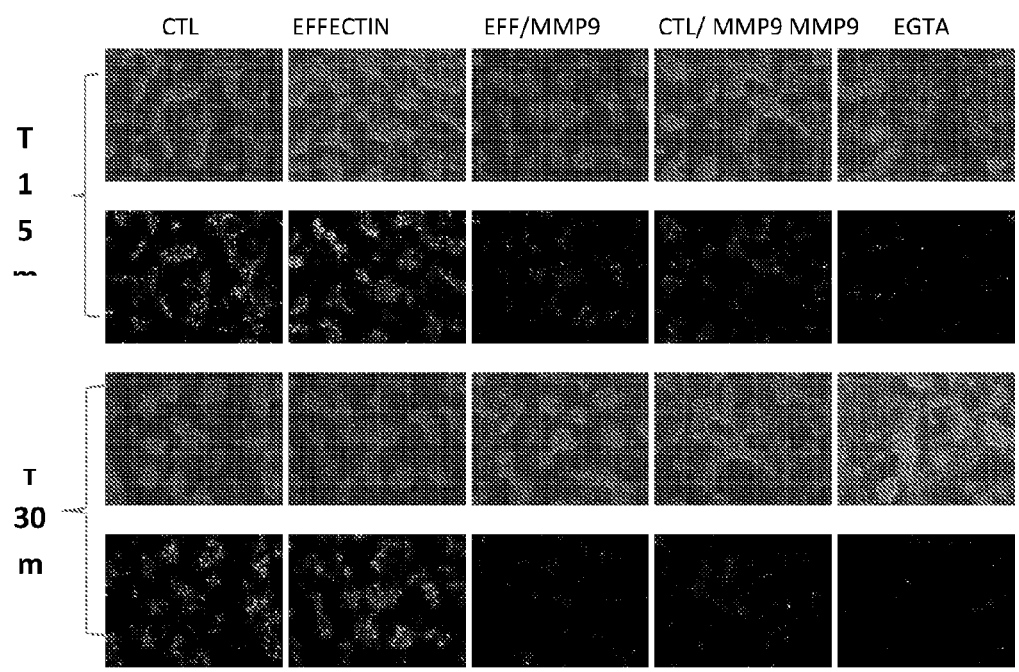
FIG. 19 is fluorescent imaging of cells exposed to activated MMP for biliary clearance of the marker compound.
Figure 20:
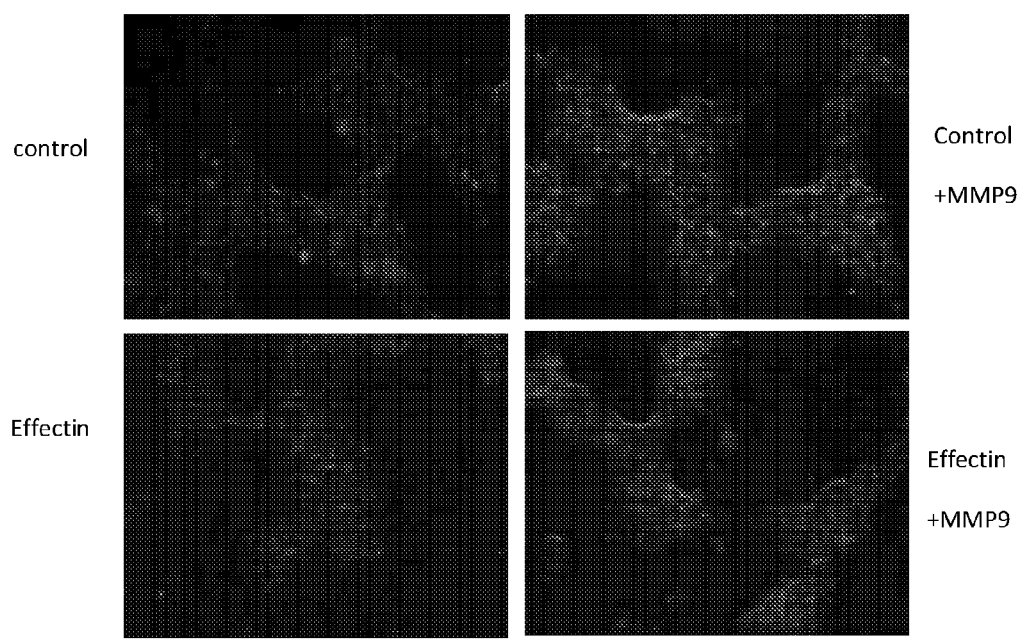
FIG. 20 is imaging of cells exposed to MMP in the presence of a large marker compound.

We also demonstrated a delay in biliary clearance in the presence of Rho-kinase inhibitor Y27632. FIG. 18 shows the rapid release of the CDFDA accumulated mainly in the canaliculi space in the control cells and a delay of the release with cells exposed to Y27632 for 30 min or 1 hour. CDFDA was added after Y27632 treatment and washing, passively entered and accumulated in all cultures for 30 min, then removed and replaced by the phenol red free culture medium. However, when the cells where exposed to MMP9, there was increased canalicular clearing efficiency of CDFDA molecules. This is shown in FIG. 19, which shows the efficiency of biliary clearance in the presence of MMP9 compared to control cells. Cells were treated with the Rho-kinase inhibitor Effectin (10 µM) for 1 hour, then washed and replaced by CDFDA solution in all wells for 30 min, then washed and replaced by medium without phenol red and added with activated MMP9 when required. Note the rapid clearance in presence of MMP9 leading us to limit the MMP9 concentration for further experiments. We further demonstrated maximal large molecules accumulation from outside the cells to canalicular space, as shown in FIG. 20. HepaRG cells were treated with Effectin for 1 hour, then washed and incubated with activated MMP9. The cells then received the BODIPY-sphingomyelin dye for 10 min., followed by observation.

DISCUSSION

Demonstration of a direct contribution of the Rho-kinase pathway in controlling morphogenesis of apical membrane polarity during hepatocyte differentiation, ductular mechanical movements and dysfunctions during cholestasis.

One main aspect of the invention is the demonstration of repeated mechanical movements of contraction and relaxation of bile canaliculi lumen formed at the biliary poles in direct relationship with the Rho-kinase pathway as a molecular regulation pathway of these movements. It was assessed by:

Demonstration of the major role of Rho-kinase in setting HepaRG hepatocyte polarity, including organization of biliary poles. Indeed, before going further in the analysis of apical lumen disorders mechanism induced in cholestatic liver tissue, differentiated HepaRG cells were submitted to analysis for their ability to recreate morphogenetic dynamics known to accompany occurrence of specific canalicular lumens as in normal human hepatocytes. Inhibition of Rho-kinase activity blocked the HepaRG hepatocyte differentiation process.

Observation of living hepatocyte colonies for 4 hours by time-lapse technical strategy, showed repeated movements of constriction and swelling of bile canalicular lumen (ex: every 45-60 min period in HepaRG hepatocytes). A direct role of these regular contraction movements onto the lumen clearing was proposed.

Evidence of a direct contribution of the Rho-kinase pathway in controlling these regular canalicular movements by using different inhibitors of the Rho-kinase itself or upstream or downstream Rho-kinase. Presence of the myosin light chain protein in its phosphorylated form (p-MLC) was associated with these movements as a consequence of Rho-kinase activity.

Another major aspect of the invention is establishment of a relationship between myosin phosphorylation, junctional complex organization and the physical barrier controlling permeability for movements of small and large molecules inside to outside the canalicular lumen. This was supported by:

Experiments aimed at inhibiting the accumulation of p-MLC using Rho-kinase inhibitors, which showed relaxation of the actiomyosin ring and swelling of canalicular lumen with reorganization in closed circumscribed vesicles;

Delay of efflux activity in these conditions, as evidenced by the time kinetics of fluorescent MRP2 substrate CDFDA efflux, also measured by using real time course of fluorescent dye released into the medium and the released radiolabelled taurocholate as an alternative;

Rapid permeability associated with recovery of efficient release activity by exposure to activated metalloproteinases (for example exposure to activated MMP9) which alter the tight junction protein complex properties.

The present invention also provides evidence for a relationship between bile canalicular activity dysfunction in cholestasis and the Rho-kinase activity alteration, and as a consequence describes two cholestatic phenotypes. It was assessed by:

Demonstration of important morphogenetic changes accompanying cholestatic disorders which can include either abnormal and permanent lumen constriction (example with chlorpromazine) or abnormal and prolonged canalicular lumen swelling (example in presence of bosentan) depending on the drug. Shape and size of the canalicular lumen are defined by using F-actin fibers deposition and accumulation forming a ring around the lumen.

Evidence of alteration of the bile canalicular functional activity as shown by the delay in bile salt precursor and/or transporter-associated substrate release outside the lumen. A set of assays has been developed to quantify specifically this canalicular activity alteration using the CDFDA-specific MRP2 transporter substrate;

Association of the morphological changes with important reorganization in the cytoskeleton observed by time-lapse imaging, creating a general disorder in the movements from cells to cells;

Association with reorganization of the junctional zones leading canalicular structures either to form closed round vesicles with a loss of repeated swelling and contraction of the lumen of these canalicular vesicles and a loss of ability to clearing, or to form huge dilated lumen pockets with also a loss of repeated movements of contractions associated with a loss of ability to clearing (a film is available for demonstration).

The data can be applied to create various assays and kits. For example, the data can be applied to:

A test for screening new therapeutical agents or biochemical, or endobiotics or food nutrients for their susceptibility to induce cholestasis, such as drugs and biochemicals which are able to direct vasopression in brain, lung vessels, muscles, etc.;

A kit to facilitate these screening assays, including for example, polarized mature HepaRG cells+F-actin+one fluorescent marker compound+MMP9 and its activator.

A screening test for characterizing cholestatic drugs in the presence or absence of target transporters, as well as a kit for the same, which would include, for example, 2 cell types, wild HepaRG and HepaRG derived cells-KO for given transporters (BSEP and/or MRP2, etc.) in order to determine the contribution of transporters in the disease;

A predicting test for cholestatic effects, using in silico approaches and taking into account the Rho-kinase pathway as a molecular control, cytoskeleton and metalloproteinases for mechanical disorders;

Test of permeability of paracellular spaces and bile duct lumen clearing for small and large molecules movements, permeability to bacteria, viruses and parasites, by using metalloproteinases markers, metalloproteinases activity and inhibitors (ex. TIMP-1) and detection of permeability by conductance measurements, permeability to calibrated labelled (ex. fluorescent) molecules, plasmids and reporter constructs; and Metalloproteinase-induced permeability as a process for favoring parasite and viral infection, transfection of plasmids or other constructs.

Matrix metalloproteinase in serum can also be used as a diagnostic marker to diagnose obstructive cholestasis in a patient. Typically, the screening test would be used for a patient who has been administered a potentially cholestatic compound and/or otherwise shows signs of cholestasis. Alternatively, the screening test could be used to identify potential cholestasis before the patient presents with cholestatic symptoms. A biological sample (e.g., blood) would be collected from the patient. The serum would be separated from the blood and analyzed for the presence of matrix metalloproteinase. The presence of matrix metalloproteinase in the serum would be a marker indicating potential obstructive cholestasis.

The invention claimed is:

1. An in vitro method of screening a candidate compound for inducing bile canalicular function disorders, said method comprising:

exposing a cell culture to said candidate compound, wherein said cell culture comprises a cell culture medium, hepatocytes and a bile canalicular structure having a biliary space characterized by a lumen;

detecting morphological alterations of the biliary space;

exposing said cell culture to a marker compound either in the presence of said candidate compound, or after removal of said candidate compound; and detecting and measuring movement of said marker compound inside and/or outside the lumen by:

exposing said culture to activated matrix metalloproteinase for release of accumulated biliary components into the medium for quantification; and calculating an amount of marker compound accumulated into the biliary space per unit time to determine the maximal amount of marker compound able to move either from the cell interior or from outside the cell to inside bile canaliculi and to accumulate into the biliary space.

2. The method of claim 1, wherein said hepatocytes are selected from the group consisting of immortalized hepatocytes, primary cultured hepatocytes, freshly isolated hepatocytes, cryopreserved hepatocytes, sandwich-cultured hepatocytes, 3-dimensional clusters of hepatocytes, HepaRG cells, and engineered HepaRG cell lines.

3. The method of claim 1, wherein said detecting morphological alterations of the biliary space comprises:
   imaging said cell culture; and
   determining changes in the size or shape of said lumen, wherein said lumen is characterized as either constricted or swollen.

4. The method of claim 1, further comprising calculating a percentage of marker compounds effluxed from said lumen per time unit.

5. The method of claim 4, wherein said detecting and measuring comprises in situ time-lapse imaging of said cell culture to detect and measure a time-dependent disappearance of said marker compound from said cells into said culture medium.

6. The method of claim 1, wherein said marker compound is a cell permeable fluorescent dye molecule of MW less than 500 Daltons.

7. The method of claim 1, wherein said marker compound is a fluorescent molecule of MW greater than 500 Daltons unable to passively enter into the cell through basolateral domains.

8. An in vitro method of screening a candidate compound for inducing bile canalicular function disorders, said method comprising:
   exposing a cell culture to said candidate compound, wherein said cell culture comprises a cell culture medium, hepatocytes and a bile canalicular structure having a biliary space characterized by a lumen;
   washing said cell culture after said exposing to said candidate compound;
   exposing said washed cell culture to a marker compound for accumulation into the biliary space to yield cell culture with accumulated marker compound;
   washing said cell culture with accumulated marker compound;
   exposing said washed cell culture with accumulated marker compound to activated matrix metalloproteinase; and
   detecting and quantifying release of said marker compound into said culture medium.

9. The method of claim 8, wherein said cell culture is exposed to said candidate compound for about 2 to about 4 hours.

10. The method of claim 8, wherein said washed cell culture is exposed to said marker compound for about 30 minutes.

11. The method of claim 8, wherein said washed cell culture with accumulated marker compound is exposed to said activated matrix metalloproteinase for from about 45 to about 60 minutes.

12. The method of claim 8, wherein said activated matrix metalloproteinase is selected from the group consisting of MMP2, MMP7, and MMP9.

13. The method of claim 8, wherein said marker compound is a fluorescent dye molecule of MW less than 500 Daltons.

14. An in vitro method of screening a candidate compound for inducing bile canalicular function disorders, said method comprising:
   exposing a cell culture to said candidate compound, wherein said cell culture comprises a cell culture medium, hepatocytes and a bile canalicular structure having a biliary space characterized by a lumen;
   washing said cell culture after said exposing to said candidate compound;
   exposing said washed cell culture to activated matrix metalloproteinase and a marker compound for accumulation into the biliary space to yield cell culture with accumulated marker compound, said marker compound being added to said cell culture during or after exposure of said cell culture to the activated matrix metalloproteinase;
   washing said cell culture with accumulated marker compound;
   incubating said cell culture for marker compound accumulation in said culture medium;
   disrupting said cell culture with a nonionic surfactant; and
   detecting and quantifying release of said marker compound into said culture medium.

15. The method of claim 14, wherein said cell culture is exposed to said candidate compound for about 2 to about 4 hours.

16. The method of claim 14, wherein said washed cell culture is exposed to said marker compound and activated matrix metalloproteinase for about 30 to about 60 minutes.

17. The method of claim 14, wherein said activated matrix metalloproteinase is selected from the group consisting of MMP2, MMP7, and MMP9.

18. The method of claim 14, wherein said marker compound is a fluorescent molecule of MW greater than 500 Daltons.

* * * * *